(12) United States Patent
Peremans et al.

(10) Patent No.: US 9,664,614 B2
(45) Date of Patent: May 30, 2017

(54) METHOD FOR HIGH RESOLUTION SUM-FREQUENCY GENERATION AND INFRARED MICROSCOPY

(75) Inventors: André Peremans, Malonne (BE); Christophe Silien, Gouvy (BE)

(73) Assignee: University of Limerick, Limerick (IE)

( * ) Notice: Subject to any disclaimer, the term of this patent is extended or adjusted under 35 U.S.C. 154(b) by 409 days.

(21) Appl. No.: 14/232,131

(22) PCT Filed: Jul. 10, 2012

(86) PCT No.: PCT/EP2012/063493
§ 371 (c)(1),
(2), (4) Date: Jul. 7, 2014

(87) PCT Pub. No.: WO2013/007726
PCT Pub. Date: Jan. 17, 2013

(65) Prior Publication Data
US 2014/0307249 A1    Oct. 16, 2014

(30) Foreign Application Priority Data

Jul. 11, 2011    (WO) .................. PCT/EP2011/061771

(51) Int. Cl.
*G01B 9/02*        (2006.01)
*G01N 21/21*    (2006.01)
(Continued)

(52) U.S. Cl.
CPC ............. *G01N 21/31* (2013.01); *G01N 21/21* (2013.01); *G01N 21/636* (2013.01); *G02B 21/06* (2013.01)

(58) Field of Classification Search
CPC ...... G01N 21/21; G01N 21/31; G01N 21/636; G01J 11/00; G02B 21/06
See application file for complete search history.

(56) References Cited

U.S. PATENT DOCUMENTS 4,360,885 A    11/1982    Edgar
5,289,407 A    2/1994    Strickler et al.
(Continued)

FOREIGN PATENT DOCUMENTS

DE    4416558 A1    8/1995
GB    2477817 A    8/2011
(Continued)

OTHER PUBLICATIONS

Gustafsson, "Nonlinear structured-illumination microscopy: Wide-field fluorescence imaging with theoretically unlimited resolution," PNAS, 102(37):13081-13086, Sep. 13, 2005.
(Continued)

*Primary Examiner* — Michael A Lyons
(74) *Attorney, Agent, or Firm* — K&L Gates LLP

(57) ABSTRACT

A method for analyzing a sample with a light probe with a spatial resolution smaller than the wavelength of the light probe comprising the steps of: —illuminating the sample by a first light pulse saturating a vibrational and/or electronic transition, said light pulse presenting an intensity spatial distribution on the sample presenting at least one minimum wherein saturation does not occur, —measuring the local absorbance properties and/or the local second order non-linear susceptibility of the sample by using a second light pulse forming the light probe at a wavelength corresponding to said electronic and/or vibrational transition, wherein the second light pulse overlap said first light pulse intensity minimum.

20 Claims, 7 Drawing Sheets

(51) Int. Cl.
  *G01N 21/31* (2006.01)
  *G02B 21/06* (2006.01)
  *G01N 21/63* (2006.01)

(56) References Cited

U.S. PATENT DOCUMENTS

| | | | |
|---|---|---|---|
| 5,479,256 A * | 12/1995 | Tamai | G01N 21/636 |
| | | | 356/450 |
| 5,731,588 A | 3/1998 | Hell et al. | |
| 6,046,925 A | 4/2000 | Tsien et al. | |
| 7,064,824 B2 * | 6/2006 | Hell | G01N 21/6428 |
| | | | 250/458.1 |
| 2003/0174560 A1 | 9/2003 | Dahmen et al. | |
| 2006/0119934 A1 | 6/2006 | O'Connell et al. | |
| 2007/0235650 A1 * | 10/2007 | Federici | G01J 3/42 |
| | | | 250/341.8 |
| 2008/0151226 A1 | 6/2008 | Hecker et al. | |
| 2008/0304046 A1 * | 12/2008 | Lee | G01N 21/1717 |
| | | | 356/51 |
| 2010/0238438 A1 | 9/2010 | Frankel | |
| 2010/0265501 A1 * | 10/2010 | Benderskii | G01J 3/4338 |
| | | | 356/307 |
| 2011/0215258 A1 | 9/2011 | Kempe et al. | |
| 2012/0097865 A1 | 4/2012 | Lippert | |
| 2012/0105854 A1 | 5/2012 | Borri et al. | |
| 2013/0256564 A1 * | 10/2013 | Hell | G01N 21/636 |
| | | | 250/459.1 |

FOREIGN PATENT DOCUMENTS

| | | |
|---|---|---|
| JP | 01232316 | 9/1989 |
| WO | 2004/090617 A2 | 10/2004 |
| WO | 2007/106069 A2 | 9/2007 |
| WO | 2010/101894 A2 | 9/2010 |
| WO | 2014/005195 A2 | 1/2014 |
| WO | 2014/106657 A1 | 7/2014 |

OTHER PUBLICATIONS

Wilson et al., "Difference confocal scanning microscopy," Optica Acta, 31(4):453-465, 1984.
Wildanger, D. et al.; "A compact STED microscope providing 3D nanoscale resolution"; Journal of Microscopy; 2009; vol. 236; pp. 35-43.
Moffitt, Jeffrey R. et al.; "Time-gating improves the spatial resolution of STED microscopy"; Optics Express; 2011; vol. 19, No. 5; (13 pages).
Lai, Ngoc Diep et al.; "Optical determination and magnetic manipulation of a single nitrogen-vacancy color center in diamond nanocrystal"; Advances in Natural Sciences Nanoscience and Nanotechnology; 2010; (6 pages).
International Search Report for PCT International Application No. PCT/EP2012/063493; Date of mailing Oct. 10, 2012; (4 pages).
International Search Report for PCT International Application No. PCT/EP2004/003767; Date of mailing Nov. 28, 2006; (8 pages).

* cited by examiner (a)

(b)

METHOD FOR HIGH RESOLUTION SUM-FREQUENCY GENERATION AND INFRARED MICROSCOPY

This application is a national phase under 35 U.S.C. 371 of International Application No. PCT/EP2012/063493 filed on Jul. 10, 2012, which claims priority to and benefit of PCT International Application No. PCT/EP2011/061771 filed on Jul. 11, 2011, the entirety of these applications are incorporated by reference herein.

FIELD OF THE INVENTION

The present invention relates to the field of microscopy with a resolution in the nanometer range. More particularly, the present invention is related to a method for chemical and structural characterization of a sample at high spatial resolution by measurement of light absorbance. The present invention is also related to a microscope implementing such a method.

BACKGROUND OF THE INVENTION AND STATE OF THE ART

Developments in biomedical research and material science rely increasingly on state-of-the-art instruments capable of structural imaging and chemical analysis at very high spatial resolution.

Far-field imaging approaches are usually diffraction limited. In the far field, chemical imaging of small features, such as nanoparticles or nanostructures which fall to a size range below 100 nm, requires thus a breakaway from the diffraction limit. A number of techniques providing chemical imaging at nanoscale resolution have been developed. However, the resolution is then either achieved using near-field techniques or in the far-field by using very short wavelengths (e.g., X-ray, electron microscopy).

In addition to nanoparticles and nanostructures, the nanometer scale is also typical of biological molecules involved in photosynthesis, color-control, and biochemical reactivity. Intracellular analysis in living cells, and the study of large biomolecules generally ranging from 10 to 200 nm, are also of interest.

Progress in these R&D fields requires the development of microscope(s) enabling the chemical characterization of materials with spatial resolution of the order of 1 to 500 nm.

The limited ability to routinely probe and understand the properties of matter at sub-cellular and at nanometer scale hinders progresses and new tools and methodologies need thus to be conceptualized and their effectiveness demonstrated.

Direct measurement of vibrational absorption by optical means requires the use of infrared (IR) beam (wavelength ranges approximately between 750 nm and 1 mm). However, contrary to ultraviolet (UV) and/or to fluorescent microscopy, which uses relatively smaller wavelengths of light (about 10-750 nm), resolutions below the micrometer range seems impossible to achieve in far-field IR microscopy, in view of the limits as expressed by the Ernest Abbe criterion, which forbids spatial resolution better than approximately half of the wavelength of the probe beam.

Chemical bonds in a molecule vibrate at a characteristic frequency. A group of atoms in a molecule may have multiple modes of oscillation. If an oscillation leads to a change in dipole in the molecule, then it will absorb a photon which has the same frequency. The vibrational frequencies of most molecules occur within the infrared light frequency ranges. Because vibrational modes are dependent on composition and on local molecular arrangement, they serve as a fingerprint of molecules, and mapping of the spatial distribution of these modes provides a mean of label-free imaging without the need for any chemically binding additives (labels). This mapping of vibrational signatures is also called chemical imaging, spectroscopic imaging or spectromicroscopy. Current state-of-the-art far-field microscopes affording a mapping of vibrational modes based on CARS (coherent anti-Stoke Raman spectroscopy), vibrational SFG (sum-frequency generation), SRS (stimulated Raman microscopy), or on IRAS (infrared absorption spectroscopy) exhibit a spatial resolution that is at best limited by diffraction.

For microscopy in Fourier Transform Infra Red Absorption Spectroscopy (FT-IRAS) mode using an IR synchrotron source the best resolution that are achieved are then limited to several microns only.

Other instrumental FT-IRAS setup using thermal sources are unable to reach these values due the poor brightness of these sources and generally the resolution is limited to about 20 microns.

Today to achieve higher resolution in IRAS it is necessary to exploit near-field scanning optical microscopies (NSOM), which require to maintain a nanoscale solid probe in the vicinity of the sample and which are thus limited to probing the surface of samples, and exhibit a large technical difficulty due to the poor reliability of probe production and to the necessity to maintain it at nanometer range from the sample. These techniques generally afford spatial resolution of the order of 100 nm.

Although NSOM afford extremely high spatial resolution in IRAS, it seems thus important to consider new techniques to achieve comparable or better resolution in the far-field, which will suppress the limitation to surface-only probing and the engineering challenges related to the nanoscale probe exploitation. However in this case, one needs to find a scheme to achieve in IRAS resolution that overcomes the diffraction limit.

The measurement of the chemical IR absorption with a resolution below the diffraction limit also cannot be done using the techniques developed for sub-diffraction far-field imaging of fluorescence emission. These relies on the controlled suppression of the fluorescence emission (e.g., STED stimulated-emission depletion), or on the localization of randomly activated fluorescent chromophores (e.g., PALM photo-activated localization microscopy, STORM stochastic optical reconstruction microscopy), or on the analysis of Moiré patterns of the emitted fluorescence (e.g., SSIM saturated structured illumination microscopy). These methods of fluorescence imaging are also not label-free since they necessitate the incorporation of fluorescent tag/label in the sample.

Since IRAS probes the intrinsic vibrational modes of molecules, it is thus label-free and it is thus extremely important to find scheme in the far-field that will afford below-the-diffraction-limit resolution for IRAS.

AIMS OF THE INVENTION

More specifically, the invention relates to breaking away from the diffraction limit of infrared absorption and related microscopy.

SUMMARY OF THE INVENTION

The present invention is related to a method for analysing a sample with a light probe at a spatial resolution smaller than the wavelength of the given light probe comprising the steps of:

illuminating the sample by a first light pulse saturating a vibrational and/or electronic transition, said light pulse presenting a spatial distribution of intensity within the sample presenting at least one minimum wherein saturation does not occur, measuring the local absorbance properties and/or the local second order non-linear susceptibility of the sample by using a second light pulse forming the light probe at a wavelength corresponding to said vibrational and/or electronic transition, the second light pulse overlapping said first light pulse intensity minimum.

According to particular preferred embodiment of the invention, the method presents one or a suitable combination of at least two of the following features:

- analysis of the sample comprises the step of structural and chemical characterization by determining the local properties of light absorption;
- the second light pulse is separated from the first light pulse in the temporal domain and illuminates the sample before the relaxation of the vibrational and/or electronic transition saturation occurs;
- the first and second light pulses present different polarization, and the measurement of the local light absorbance properties and/or the local second order non-linear susceptibility of the sample comprises the step of filtering out the polarized signal arising from the first light pulse by means of a polarizing filter;
- the first and second light pulse are angularly separated so that the signal arising from the first and second light pulses are angularly separated;
- the first and second light pulse are separated by means of time-gating, preferably an optically triggered non-linear SFG up-conversion;
- the transition is non-fluorescent;
- the first and second light pulses are infrared light pulses, preferably having a wavelength comprised between 1 and 50 µm;
- the sample is further illuminated by visible light and wherein the detection is performed by Sum-Frequency Generation (SFG);
- the detection is performed by IR absorption spectroscopy;
- the spatial resolution is about 1000 to 5 nm, preferably of about 100 to 10 nm;
- the second light pulse have a wavelength equal to the wavelength of the first light pulse (i.e. the wavelengths are sufficiently close to be absorbed/saturate the same vibrational/electronic transition);
- the intensity minimum of the first light pulse is induced by an interference device producing-intensity nodes;
- the first light pulse has a duration comprised between 10 fs and 100 ps, preferably between 500 fs and 20 ps, more preferably about 1 ps;
- the intensity of the first light pulse is higher than about 0.2 $nJ/\mu m^2$, preferably higher than 2 $nJ/\mu m^2$, more preferably higher than 20 $nJ/\mu m^2$;
- the duration of the second light pulse is comprised between 10 fs and 100 ps, preferably between 500 fs and 20 ps, more preferably about 1 ps;
- the method is repeatedly applied at a repetition rate lower than 10 MHz;
- the repeated first and second light pulse are scanned in two directions on the sample surface to be able to reconstruct an image of the absorbance and/or second order susceptibility of the sample surface.

A second aspect of the invention is related to a microscope comprising:

- at least one light source able to illuminate a region of interest of a sample by a first and a second light pulse, said first light pulse being able to saturate a vibrational and/or electronic transition,
- first optical means arranged so that the first light pulse presents, in use, at least one minimum of light intensity on the sample,
- second optical means arranged so that the second light pulse overlap said at least one minimum,
- detection means for determining absorbance and/or second order non-linear susceptibility of the sample using the second light pulse,
- said second light pulse having a wavelength corresponding to said vibrational and/or electronic transition, characterized in that the microscope further comprises means for reducing in use the signal arising from the first light pulse on the detection means by timely separating, angularly separating and/or polarizing in different directions, the first and second light pulses or by using slightly different wavelength of the first and second light pulses.

According to particular preferred embodiment the microscope of the invention further comprises one or a suitable combination of the following features:

- said at least one light sources is arranged so that the first and second light pulses are timely separated when reaching the sample surface;
- the at least one light source comprises at least one pulsed laser;
- the at least one light source comprises one pulsed laser, a beam splitter device such as a partially reflective mirror or a polarizer for splitting each laser pulse into said first and second light pulse, the second light pulse being delayed by optical means from the first light pulse for sequentially illuminating the region of interest by the first and second light pulse;
- the first optical means comprise an interfering device on the optical path of the first light pulse for inducing light intensity minima of the first light pulse on the sample;
- the first and second light pulses consist of infrared light;
- the first and second light pulses are infrared light pulses and the microscope further comprises a visible light source for determining the second order non-linear susceptibility of the sample by measuring a sum frequency generation signal;
- the microscope of further comprises scanning means for synchronously displacing the intensity minimum of the first light pulse and the position of the second light pulse;
- the microscope further comprising scanning means for synchronously displacing the sample relative to the laser beams.

Advantageously, the method of the invention does not require heat transfer nor refractive index change nor fluorescent transition.

Advantageously, in the method of the invention, the first light pulse induces a local decrease of the absorbance of the sample and/or the non-linear susceptibility of the said sample.

The method of the present invention is especially well suited for the analysis of crystalline (non amorphous) sample(s).

Advantageously, in the method of the invention, the local infrared absorbance of the sample is measured with spatial resolution smaller than a quarter of the light probe wavelength and/or the vibrational signature of the sample is measured with spatial resolution smaller than a quarter of the infrared probe source wavelength.

Possibly, in the method of the invention, the light probe used has a wavelength laying in the UV-visible-near infrared spectral range between 0.2 to 1.5 µm.

The at least one minimum of intensity of the first light pulse can be defined in the 2 dimensions defined by the sample plane for scanning the sample in two dimensions, the absorption of the sample being averaged in depth, or, as described in the Journal of Microscopy, Vol. 236, Pt 1 2009, pp. 35-43 by Wildanger et Al. for STED measurements, the at least one minimum can also be resolved in depth, so that three dimensional images can be obtained by scanning the sample in three dimensions.

A related aspect of the present invention is a device for microscopy comprising at least a first emission source generating an optical beam, named hereafter the "saturating" beam, and at least a second emission source generating at least one optical beam, named hereafter the "probe" beam, wherein the "saturating" beam excites a vibrational or electronic transition in the material to be analysed, and wherein the "probe beam" measures locally the absorption property or the second order non-linear susceptibility property of the material, and wherein the spatial distribution of the "saturating" beam intensity increases the spatial resolution of the local analysis of the material property by modifying locally its absorption or second order susceptibility.

In this device, two probe beams, one in the visible spectral range, and one in the infrared spectral range are used to measure the local vibrational signature of the material by sum-frequency generation and/or the "saturating" beam is an infrared beam, which (is able to) excites a vibrational transition of the material to be analysed.

Alternatively, in this device, the probe beam is infrared and is used to measure the local IR absorbance of the material to be analyzed, and/or the "saturating" beam is infrared and excites a vibrational transition in the material to be analyzed.

Preferably, in this device, the saturating beam spatial intensity distribution is shaped to present a minimum in its centre in spatial overlap with the probe beam maximum intensity.

The method of the invention advantageously allows for below-the-diffraction-limit IRAS microscopy, preferably with a lateral resolution below 100 nm. Such Infra Red Nanoscopy (IRN) and/or Sum Frequency Generation Nanoscopy (SFGN) on table-top portable architecture are far superior to the state-of-the-art IRAS imaging that requires synchrotron and works at best at diffraction limited resolution of several microns.

The microscopy techniques of the invention can be generically defined as Absorption Saturation Microscopy (ASM), IRN and SFGN being particular cases of this general technique and sometimes defined ASM IR or ASM SFG.

DETAILED DESCRIPTION OF THE INVENTION

Figure 1:
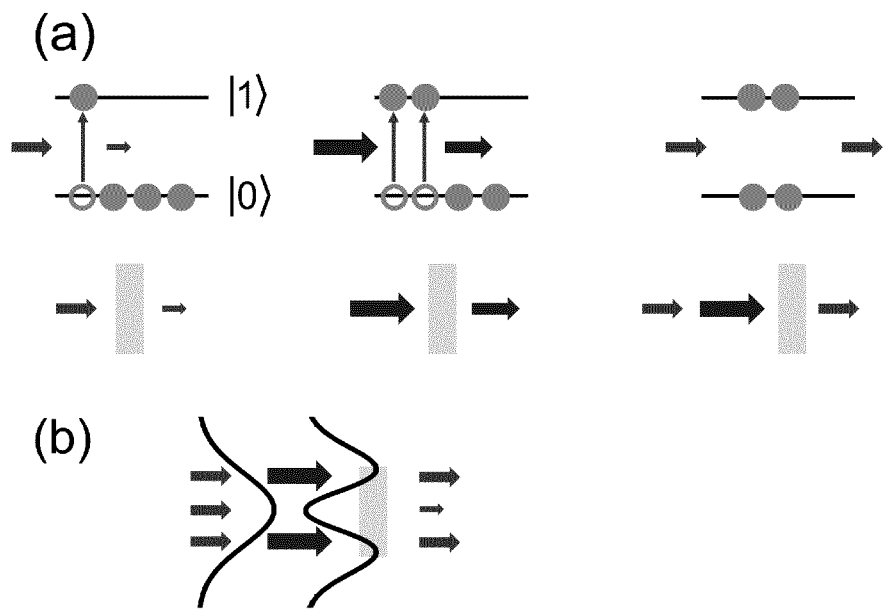
FIG. 1 represents a schematic description of the physical principle of the invention.

The present invention enables to overcome the diffraction limit in infrared absorption and SFG microscopy.

The present invention proposes a concept for measuring the IR absorption by vibrational modes in a below-the-diffraction limit region of the sample.

The present invention further presents the advantage of working in the far-field, and is applicable to the analysis of different interfaces (solid-air, liquid-solid, liquid-air, liquid-liquid), biologically relevant samples, and other nano-materials.

The device of the present invention enables measuring vibrational signature in samples with spatial resolution more than a decade better than achievable with current state-of-the-art synchrotron-based infrared microscopy.

The device also permits local absorption spectra to be measured in the visible range.

The device relies on the saturation of an optical transition.

The device of the present invention aims at saturating a sample optical transition, which can be vibrational and/or electronic, by a 'saturating' pump pulse, and to subsequently 'probe' it by Sum-Frequency Generation (SFG) or absorption (infrared, visible or UV) spectroscopy (being preferably IR) using a second light pulse (light probe). In alternative embodiments, or in combination with time separation, the pump beam and the probe beam can be spatially separated (angularly) or separated by using different polarization for the pump and the probe, or by time-gating.

Explanation of the mechanism illustrated in FIG. 1a: the FIG. 1a illustrates the well-known concepts of IR absorption spectroscopy (IRAS) and of IR pump-probe spectroscopy, for which both pump and probe pulses are tuned to the wavelength of the vibrational transition, in the IR thus. (FIG. 1a left) A pulse of low intensity undergoes partial absorption within a ensemble or sample of two level systems (i.e., molecules or part of a molecule) and the linear absorption of each quanta of light or photon leads to the excitation of one oscillator from the ground state $|0\rangle$ to the excited state $|1\rangle$.

Competition between stimulated absorption and emission processes prevent the population of $|1\rangle$ to exceed that of $|0\rangle$, so that a pulse of very high intensity excites at most half the oscillators (FIG. 1a centre). The latter situation is defined as the sample saturation. In the pump-probe experiment (FIG. 1a right), the same pulse of very high intensity (i.e., enough to saturate the sample) is immediately followed by a delayed probe pulse which does not undergo any absorption for pump-probe delays shorter than the lifetime of $|1\rangle$.

In other words, the second pulse probes the population of the sample and regions of the sample irradiated by the pump are virtually 'transparent' to the probe at short pump-probe delays.

The concept of ASM (or ASM IR or IRN) is depicted in FIG. 1b. The 'saturating' (pump) beam irradiates the sample with an intensity pattern with intensity minima or extinction (nodes). This pump profile is for example readily achieved using a vortex phase plate.

A Gaussian shaped probe, delayed by a time shorter than the lifetime of $|1\rangle$, irradiates the sample and is transmitted with little change where the intensity of the 'saturating' (pump) beam is sufficient to saturate the sample. The transmitted Gaussian probe is reduced where the intensity of the 'saturating' (pump) beam is null or not sufficient to saturate the sample.

The energy of the outgoing probe pulse is measured by a detector (integrating device), and the absorbance of the sample in the node of the 'saturating' (pump) beam is readily inferred by subtracting the measured energy from the energy of the outgoing probe pulse in the absence of sample. The result of the difference is called the ASM (or IRN or ASM IR) signal. The IRN image is generated by plotting the IRN signal for different position of the sample within the pump and probe beams.

The probe pulses can be either the combination of two pulses, one visible and one infrared, in the case of SFG, one IR pulse in the case of IRAS, or one visible pulse in the case visible-UV absorption spectroscopy.

The sub-diffraction resolution results from the non-linearity of the 'saturation' and thus of the quenching of the second order non linear susceptibility or of the absorbance of the sample with respect to the local optically patterned 'saturating' pump pulse intensity.

The principle is illustrated numerically in the case of SFG and IR absorption spectroscopy in the following FIGS. 2 and 3.

Figure 2:
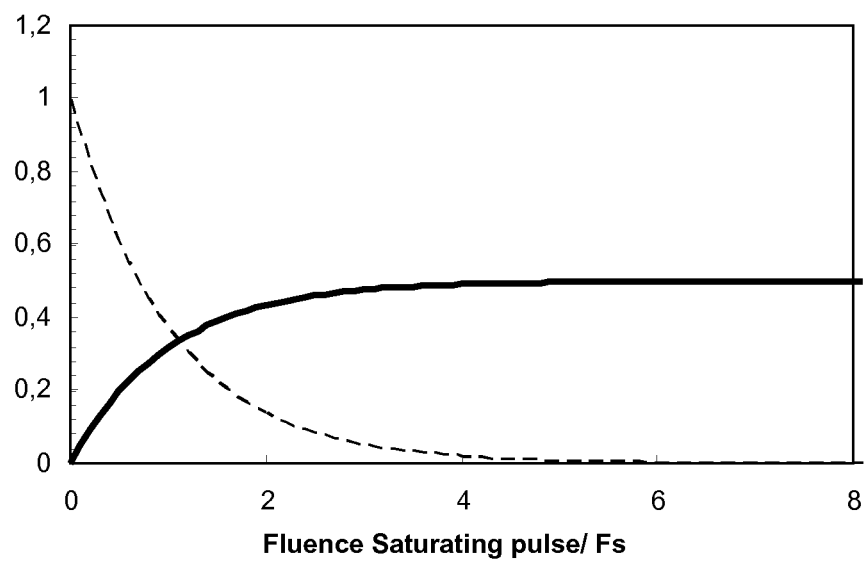
FIG. 2 represents the excitation probability (continuous lines) of a vibrational transition as a function of the saturating light pulse fluence and the quenching (dashed line) of the IR and SFG cross section.

FIG. 2 shows the excitation probability of a vibrational transition at 3 µm, modeled as a two level system, irradiated resonantly by an infrared laser pump pulse. The thick black curve is calculated in the Markov approximation, i.e. by neglecting Rabi Oscillations and vibrational relaxation. This curve verifies $$N_1 = \frac{1 - e^{-CF}}{2}, \quad (1)$$

where $N_1$, is the excited level population and F, the fluency of the 'saturating' pump pulse. From equation (1), the inventors define the saturation fluency $F_s$ as:

$$F_s = \frac{1}{C}. \quad (2)$$

The saturation of the vibrational transition induces the quenching of the its susceptibility for SFG and IR absorption spectroscopy, as shown in FIG. 1 by the discontinuous lines which obeys the following equation, respectively:

$$Abs_{IR} \sim \left(\frac{1}{2} - N_1\right) \quad (4)$$

Although it is not a unique experimental configuration, for this numerical illustration, the inventors use a simple interference pattern, generated by dividing the "saturating" pulse in two and focusing the resulting beams in a counter propagating geometry on the sample, to illustrate the concept of IRN. These "saturating" beams will generate on the sample a stationary wave with intensity extinction nodes separated by half the wavelength used, that is 1.5 µm if the inventors select a wavelength of 3 µm typical for vibrational excitation in organic samples, as shown by the thick curve in FIG. 3. FIG. 3 also shows the SFG and IR absorbance (discontinuous line) profiles for the same vibrational excitation after saturation and prior to de-excitation.

The sample parts (for example molecules) with a vibrational mode at 3 µm, and situated in the maximum intensity of the "saturating" stationary wave will be saturated and consequently their IR absorbance and/or SFG cross section will be quenched. Therefore the discontinuous curves represent the local contribution to the SFG and IR signals, as a function of their position in the "saturating"—(or "quenching" or pump) pattern.

Figure 3:
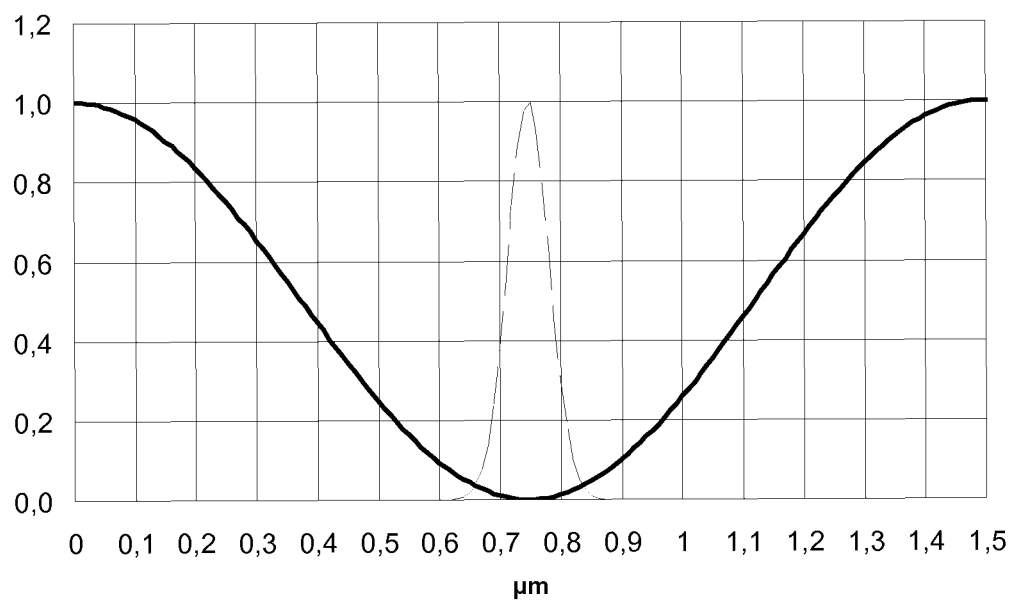
FIG. 3 represents an example of intensity profile of the first light pulse (thick line) and the corresponding IR absorption or SFG sensitivity profile (dashed line).

The curves in FIG. 3 have been calculated assuming that fluency at the maxima of the "saturating" (pump) patterns is 100 times higher than Fs., defined in equation (2). In such condition, the inventors observe that a spatial resolution of 60 nm (full width at half maximum) is achieved. In similar condition, but the "saturating" (pump) maxima only 10 times higher than Fs, the achieved spatial resolution would still be ~150 nm.

The inventors have developed a set of characteristics for the ideal laser for IRN. First, the "saturating" pump beam must be focused at the diffraction limit on the sample. For a pump beam at 3 µm, with diameter of 25 mm, focused using a lens of focal length 50 mm, at 65 deg incidence on the sample, the inventors obtain an elliptical spot of 10 µm×23 µm, equating to 230 µm².

The inventors have saturated CH and CO vibration modes with 10 ps long pulses and fluency level of 40 nJ per 230 µm². The IRN method requires therefore in those cases IR pulses with energies of the order of 4 µJ per 230 µm².

The probe pulses for SFG or IR absorption spectroscopy can be (should be) much below the saturation level, e.g. of the order of 10 nJ.

The weak SFG signal or IR absorption signal, per pulse, must be compensated by a high repetition rate in order to obtain a globally measurable signal for nanoscale sample volumes. The repetition rate is preferably limited to 5-30 MHz, preferably to 5-15 MHz, and more preferably to about 10 MHz, because of the sample temperature relaxation time. The IR probe beam power can therefore be of the order of 50-300 mW, preferably 50-150 mW, and more preferably ~100 mW and will permit to generate SFG signal intensities comparable to these obtained with existing SFG setup dedicated to microscopic samples.

The saturating-quenching beam for the IRN or SFGN (ASM-SFG or ASM-IR absorption spectroscopy), should be achieved from infrared picosecond pulses of duration of the order of 1 to 10 ps (with bandwidth of about 10 to 1 cm$^{-1}$, close to the Fourier transform limit), pulse energy of the order of 4 µJ, and high repetition rate in the range of 1 kHz to 10 MHz, corresponding to an average power between 0.004-40 W.

This example of specifications demonstrates that the technology of synchronously pumped optical parametric oscillator (OPO) built around periodically polled LiNbO$_3$ crystals, and pumped by fiber lasers or Ti-Sapphire regenerative amplifier can fulfill the requirements for IRN. The specifications are not unique. Higher energy pulses, with lower repetition rates, can be also be used for chemical imaging of larger samples using more complex 'saturating' interference patterns.

Figure 4A:
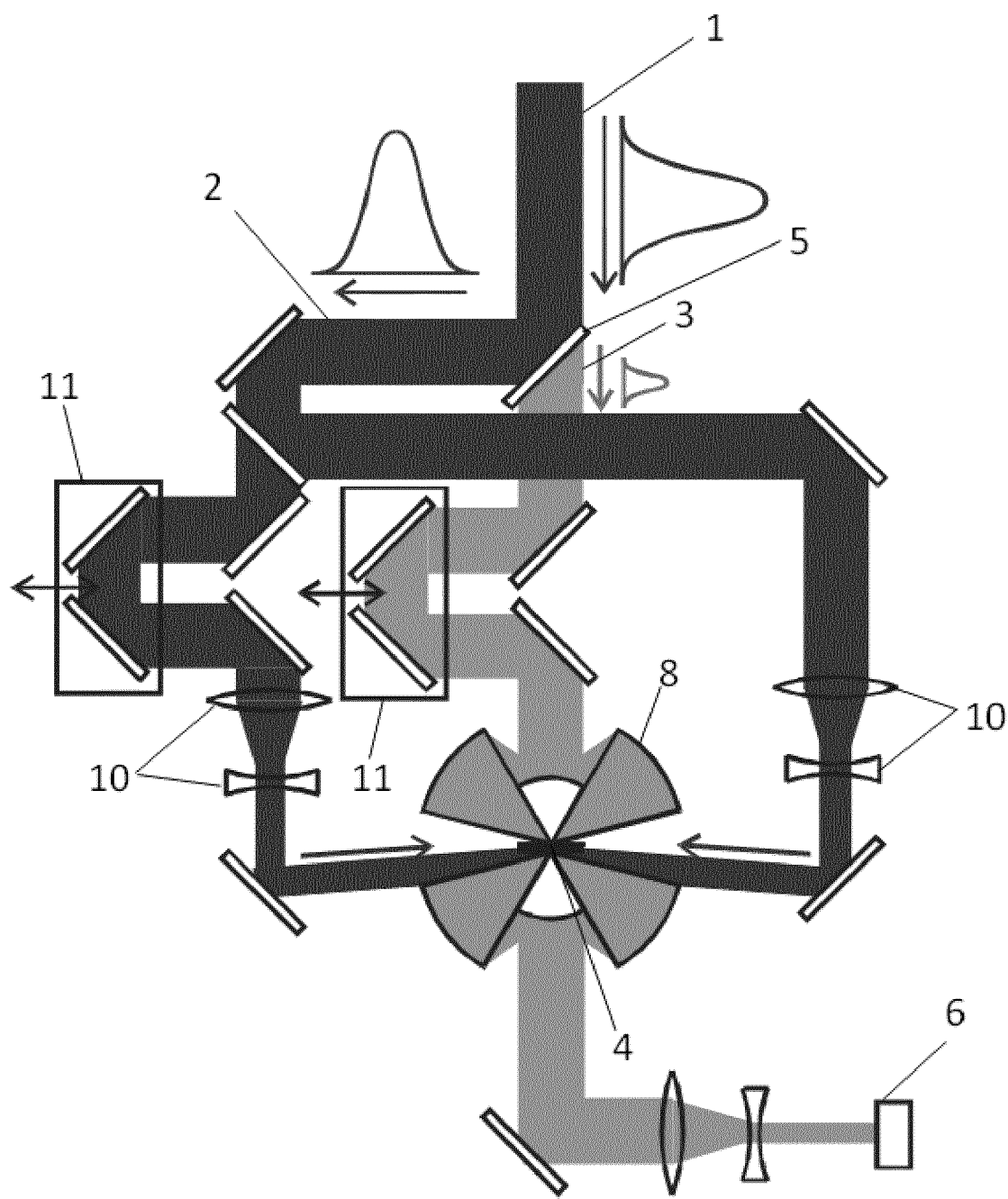
FIGS. 4 a, b and c schematically represent examples of microscope according to the invention.

FIG. 4a schematically represents an example of a microscope according to the invention. In such a microscope, a pulsed laser beam 1 is splitted into a first pulsed "saturating" laser beam 2 and a second pulsed "probe" laser beam 3 by means of a beam splitter 5. The "saturating" and "probe" laser beams are focused onto the sample 4 by means of lenses or Schwarzschild objectives 8,10. The synchronization of respective delay between the "saturating" and "probe" beams is adjusted using a delay line 11.

The ratio of the light intensity transmitted through the beam splitter on the light intensity reflected by the beam splitter is defined by the intrinsic reflectivity of the beam splitter 5. Preferably, in the invention, the first beam represents 90 to 99% of the total light.

In order to define an intensity minimum in the "saturating" beam intensity distribution, interference is used. In the example of FIG. 4a, the interference is obtained by generating a standing wave using two counter propagating beams.

Finally a detector 6 is used to measure the signal of interest.

In order to simplify the synchronization of the x-y displacement of the first and second pulsed laser beam relative to the sample 4, it is preferably the sample 4 which is displaced in x-y directions relative to the pulsed beams. This may be done for example by using piezoelectric sample holder, such as those used in near field microscopy (AFM, STM . . . )

Figure 4B:
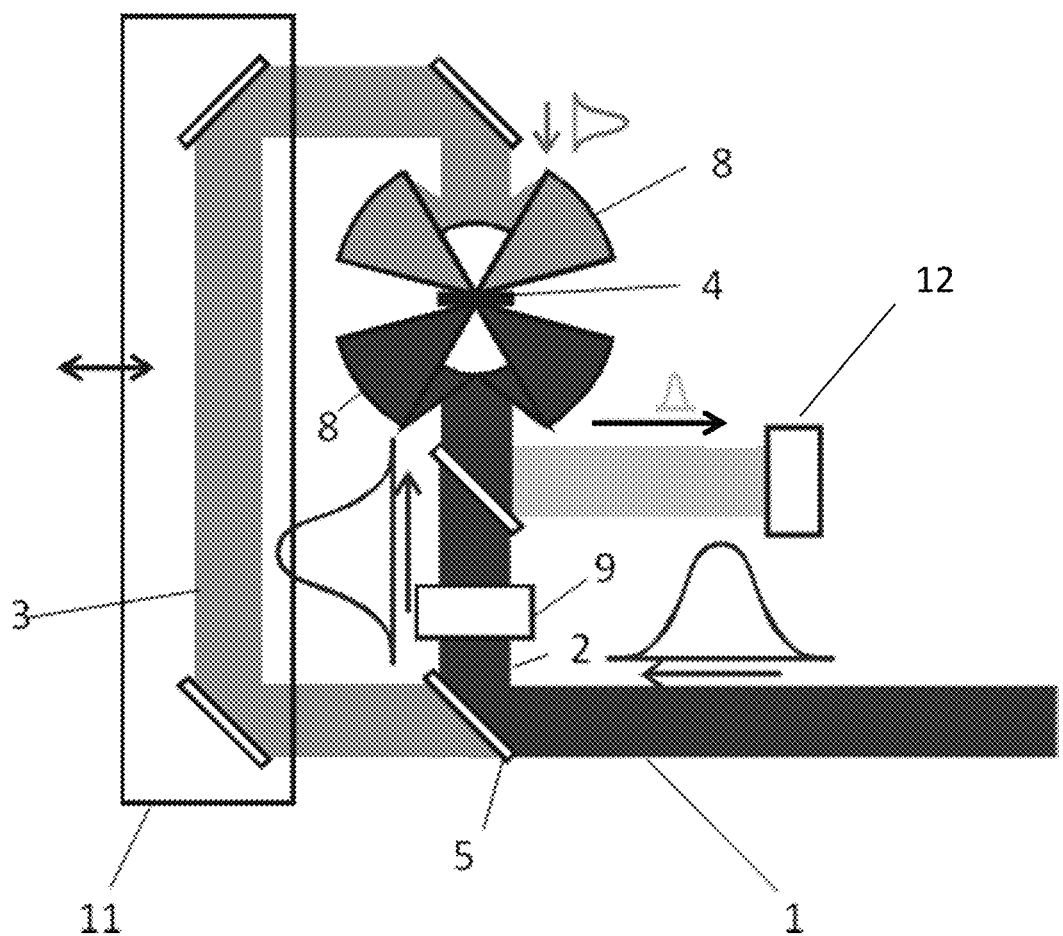

FIG. 4b represents another example of microscope according to the invention wherein the "saturating" (pump) and "probe" pulse are counter-propagating in the sample. The interfering device 9 is possibly a vortex wave plate that will generate a doughnut intensity profile of the saturating pulse intensity in the focal plane of the sample. Mirror 12 must be only slightly reflective to steer part of probe pulse towards the detector while being highly transparent to the saturating pulse.

Figure 4C:
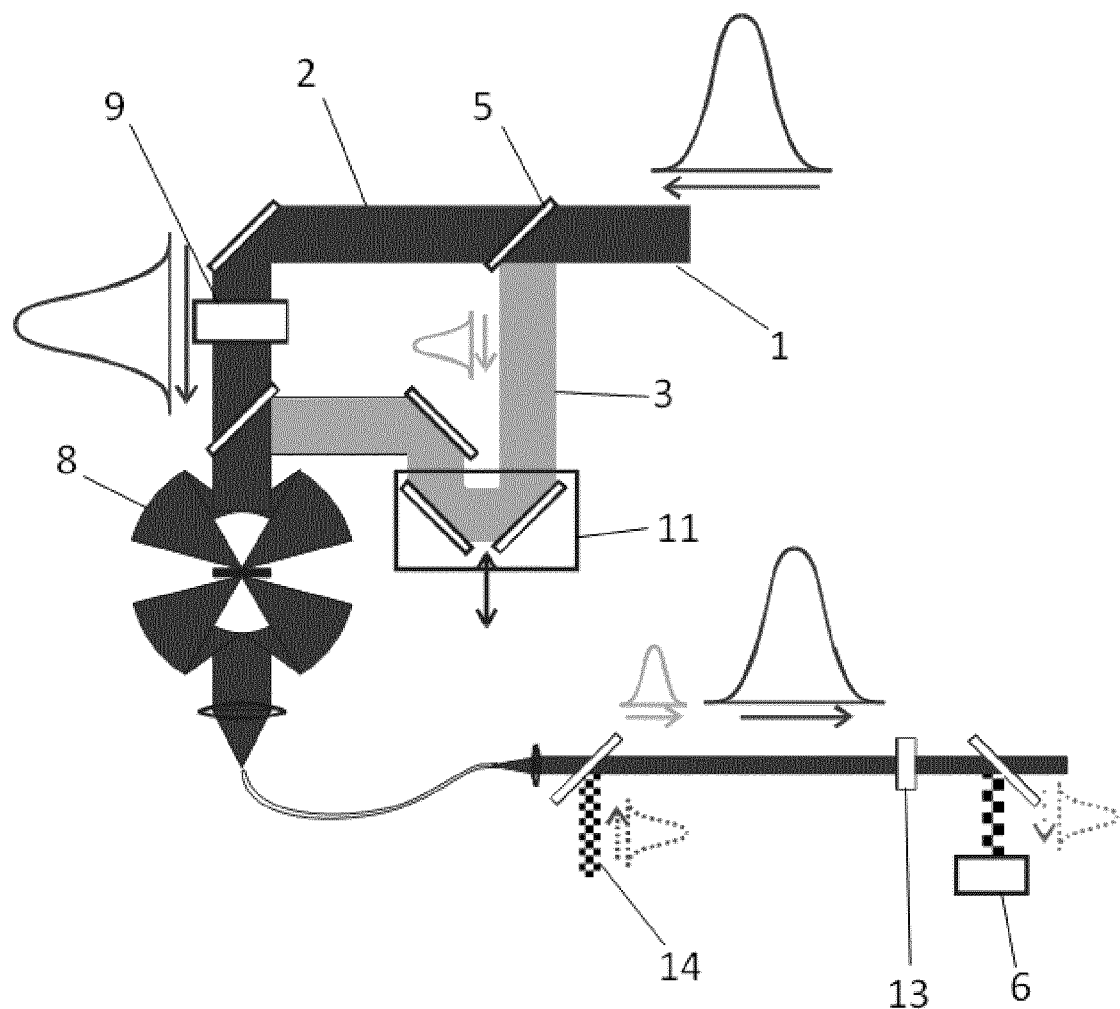

FIG. 4 C represents another example of microscope according to the invention where the "saturating" (pump) and "probe" pulse are co-propagating towards the sample. The probe pulse can possibly be selectively detected using synchronous (time-gated) detection, by means of a non-linear process such as sum frequency generation in a non-linear material 13 with a reference pulse 14.

EXAMPLE

The following example illustrates how to use the method to record the IRN (or ASM IR) signal.

This example illustrates a computed simulation of the mapping of a vibrational mode absorption with a resolution below the diffraction limit, and defines an example of IRN point-spread function (PSF). To define the PSF in this example, one uses two different intensity profiles for the pump and one records/integrates the intensity/energy of the probe in both cases.

The difference between probe intensities is defined in this example as the IRN signal and has a PSF that is punctual and has a below-the-diffraction-limit full-width at half maximum (i.e., the fwhm is a measure of the microscope resolution). The discussion concerns a measure in transmission geometry but also applies to a measure in reflection geometry.

The following IRN PSF simulation uses a simplified model of Einstein for the absorption.

A sample corresponding to a self-assembled film of octadecylsilane is used in this realistic case-study of an organic thin film. The sample has been patterned in such a way that the molecules are confined in a region of 25×25 nm$^2$. That dimension is small with respect to the expected resolution for IRN, and thus computing the IRN images will provide a simulation of the PSF (i.e., the image of a small punctual object). The fwhm of the PSF is a direct measure of the resolution.

The sample is modeled in space as an ensemble of voxels (volumetric pixels, or 3D pixels) containing each a collection of independent oscillators and the temporal evolution of the relative population density N of the oscillators in the excited state $|1\rangle$ reads in Cartesian coordinates:

$$\frac{dN}{dt} = -\Gamma(r)N(r) - \beta(r)\Delta N(r, t)I(r, t), \quad (5)$$

where $\Gamma$ is the deexcitation rate of $|1\rangle$, $\beta$ is the stimulated emission/absorption Einstein coefficient, $\Delta N$ is the difference in relative population density between the levels $|1\rangle$ and $|0\rangle$, I(r,t) is the local intensity at a given sample voxel, r=(x,y,z) is the voxel position with z the coordinate along the propagation axis and (x,y) the coordinates in the sample plane, and t is the time. The intensity is computed from:

$$\frac{dI}{dz} = \frac{hc}{\lambda}\beta(r)\rho(r)\Delta N(r, t)I(r, t), \quad (6)$$

with h and c the Planck constant and the speed of light in vacuum, and $\rho$ is the density of oscillators in a given voxel.

A Mathlab code was used to solve the system of equations, developed using the backward Euler approach and independently for each set of (x,y) coordinates. The solution is readily found by iteration with the boundary conditions N(r,t$_0$)=0, where t$_0$ is a reference time before irradiation of the sample, and I(x,y,z$_0$,t) describing the temporal evolution of the intensity impinging the sample at z$_0$ (i.e., for co-propagative pump and probe pulses in transmission).

The departing probe pulse energy $\Sigma$ was computed by integrating the intensity in the sample plane (x,y) and over time, at the coordinate z exceeding the sample thickness. IR absorption images and sub-diffraction IRN images were computed by repeating the calculation whilst varying the relative position of the sample with respect to the pulses. The IR absorption (i.e., diffraction limited image of the IR absorption) and the IRN images are defined respectively by $$IR(\%) = \frac{\sum(z_0) - \sum}{\sum(z_0)} \times 100 \quad (7)$$

and $$by\ IRN(\%) = \frac{\sum_{Gauss} - \sum_{vortex}}{\sum_{Gauss}} \times 100, \quad (8)$$

where $\Sigma(z_0)$ is the probe pulse energy incident on the sample, and $\Sigma_{Gauss}$ and $\Sigma_{vortex}$ are the probe pulse energy transmitted through the sample following a Gaussian or a vortex (i.e., nodal profile, see below) pump pulse, respectively. The calculation neglects scattering and diffraction in the sample, which is justified since its thickness is of a few microns maximum, and thus typically shorter than the wavelength, and since the whole transmitted intensity is integrated over the sample plane.

In the focal plane, the spatio-temporal intensity profile of the Gaussian pulses (i.e., zeroth order) is defined by $$h_{Gauss}(r,t) = h_{Gauss}^0 e^{-r^2/w_0^2} e^{-(t-\Delta t)^2/\tau_0^2} \quad (9)$$

where $r$ and $\theta$ are the polar coordinates in the plane normal to the direction of propagation, and where the full width at half maximum (fwhm) of the Gaussian is defined by $2\sqrt{\ln(2)} w_0$ ($w_0$ being the Gaussian waist) and a temporal pulse duration by $2\sqrt{\ln(2)} \tau_0$. $h_{Gauss}^0$ is a constant adjusted to reproduce pulse energies ranging from 1.0 nJ to 1.0 µJ for the Gaussian pump pulses and 0.1 nJ for the probe. $\Delta t$ is zero for the pump pulses and set to a finite value for the probe, marking the pump probe delay.

The nodal intensity profile is set to that of a vortex whose wavefront evolves has a spiral along the direction of propagation and that corresponds to a first order Gaussian mode. The intensity in the focal plane is written $$h_{vortex}(r,t) = h_{vortex}^0 r^2 e^{-r^2/w_0^2} e^{-(t-\Delta t)^2/\tau_0^2} \quad (10)$$

with $h_{vortex}^0$ adjusted to the desired pump energy. These profiles are experimentally achieved by inserting in the beam path of an originally Gaussian pulse a vortex phase plate, inducing a progressive change of phase of $2\pi$ for a complete rotation of $\theta$. Such vortex phase plates are for example commercialized by RPC Photonics (Rochester, N.Y., U.S.A.).

Aiming to a realistic prediction of the IRN microscopy performances, the fwhm of the pulses were adjusted to those expected with objectives of numerical aperture (NA) 0.7 and 0.85. The first value is chosen because it is the maximum reported NA for reflective objective and is used in synchrotron IR absorption microscopy and the second value because IR lenses at 3.5 µm with a NA of 0.85 are commercially available. Although better resolution is expected for larger NA value, the achromatic behavior of the reflective objectives makes them of very high interest in IR absorption microscopy. At the diffraction limit, these objectives focus a Gaussian beam ($\lambda$ at 3.5 µm) to a spot of fwhm ca. 2.4 and 1.9 µm, respectively. The beam waist $w_0$ defined above is adjusted to these expected fwhms.

Pump-probe spectroscopy of vibrational modes is best achieved with picosecond-long pulses, affording suitable time resolution without compromising too much on the spectral resolution. A duration of 1.0 ps was then chosen for all pulses.

Figure 5:
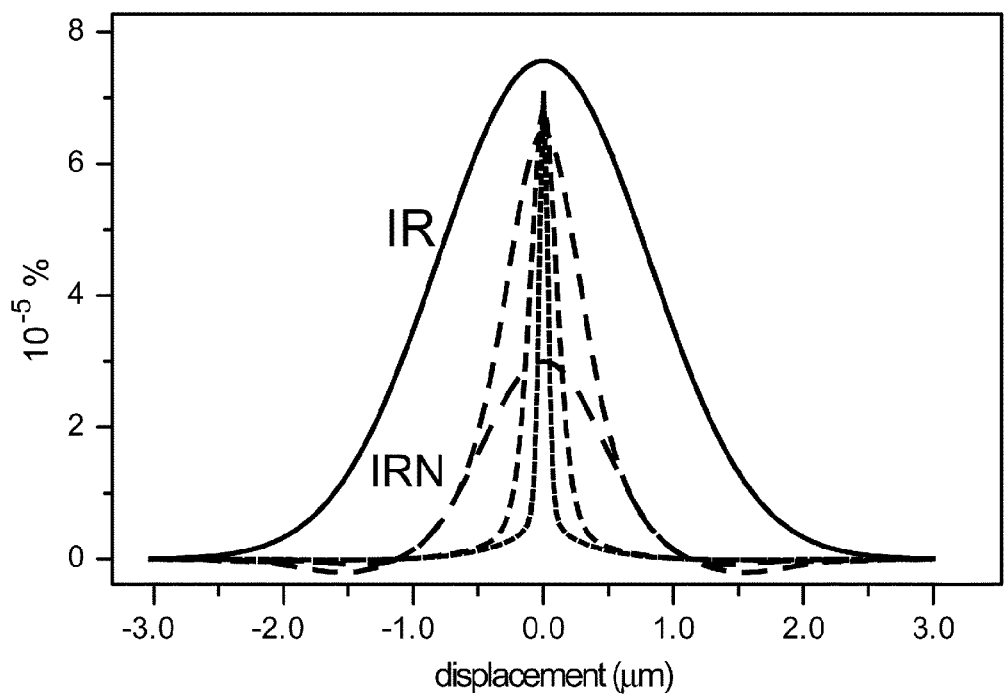
FIG. 5 graphically represents the resolution obtained when using an example of the invention as a function of the pump pulse energy (shorter dash for higher energy), compared with prior art resolution (broad curve, continuous line).

As shown in FIG. 5, the diffraction limited PSF for IR absorption microscopy (state of the art synchrotron IRAS) exhibits a fwhm of 1.9 µm, equivalent to that of the probe. The fwhm for IRN is on the other systematically below the diffraction limit and down to ca. 100 nm for a pump of 1 µJ.

Figure 6:
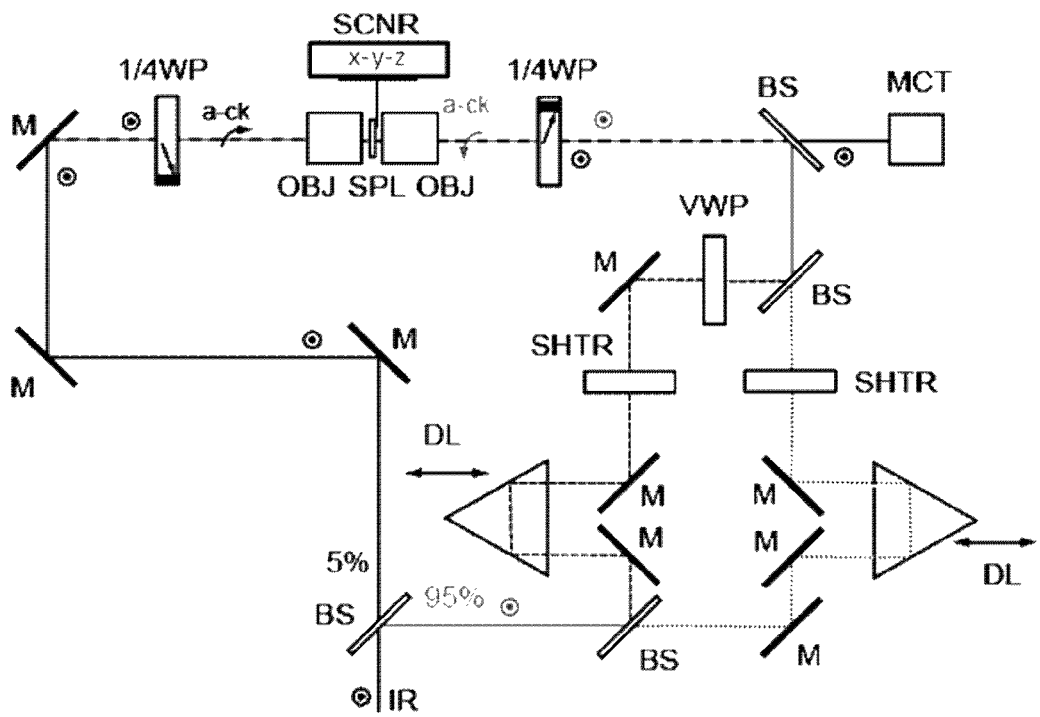
FIG. 6 schematically represents the geometry of the device used in the example of FIG. 5. (keys: M mirror, BS beam splitter, DL delay line, OBJ objective, SPL sample, SCNR scanner, MCT detector in the IR, SHTR shutter, ¼WP quarter waveplate, VWP vortex phase plate).
Figure 7:
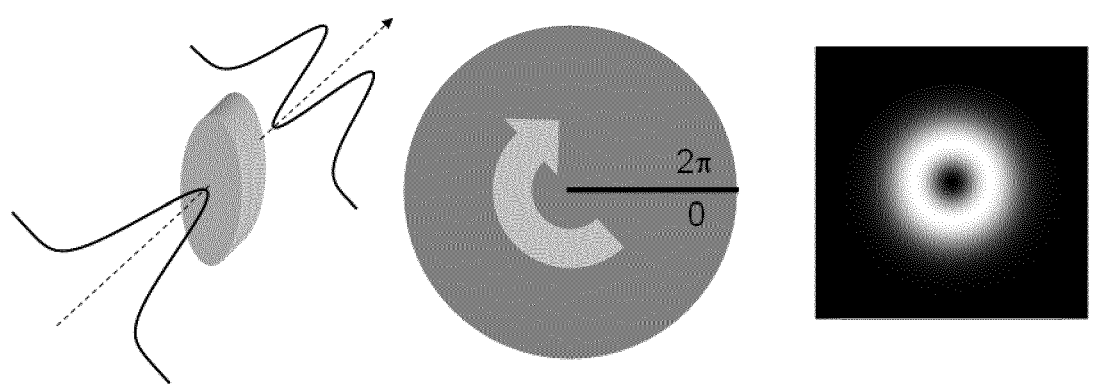
FIG. 7 represents an example of geometry of wave plate (VWP, vortex phase plate) inducing a doughnut like intensity distribution as described in the example.
Figure 8:
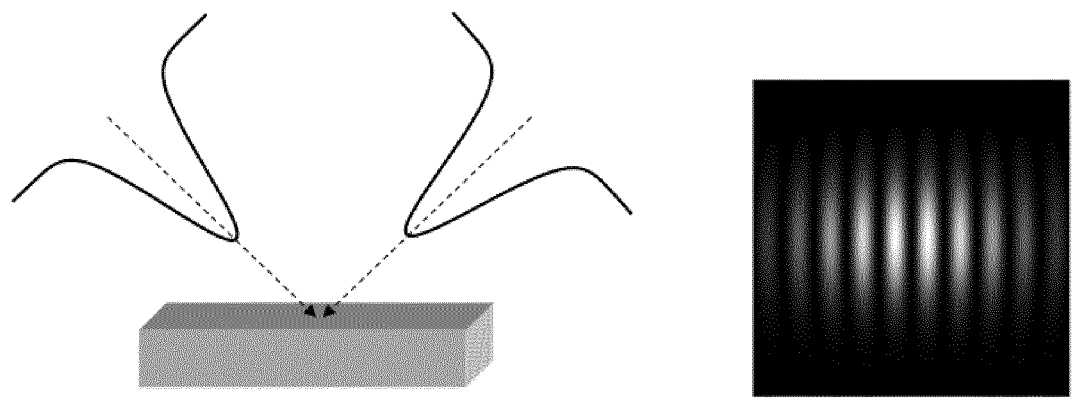
FIG. 8 represents an example of interference geometry inducing periodical intensity minima, which can be used in the method and the device of the invention.

The proposed example of embodiment affords thus the generation of a PSF without the need for generating any further reference measure. A schematic of the exemplified IRN microscope is described in the FIG. 6 for counter-propagative pump and probe pulses.

The sample absorbance/IRN signal is measured in transmission and placed between two high NA objectives (preferably but not necessarily reflective objective). The sample is placed on a scanner (alternatively the beam can be scanned).

The IR laser (tuned to the vibration wavelength) is split to create the pump and probe beams. The path of the pump beams (split again in two) are adjusted to be a little shorter than the probe one using the delay lines. One pump beam is shape to a nodal profile using a vortex phase plate. Rapid shutter allows for selecting either of the two pumps.

The pumps are counter-propagative with respect to the probe (possible for a transparent sample). The probe is detected by a detector and the signal integrated. An imaged is generated by recording the difference of the values at the detector for each pump whilst scanning the sample with respect to the pump/probe beams. A lockin amplifier can be used for measurement of the said difference.

The invention is also described in the priority document PCT/EP2011/061771 which incorporated herein by reference.

The invention claimed is:

1. A method for analyzing a label-free sample with a light probe with a spatial resolution smaller than the wavelength of the light probe comprising the steps of:
    illuminating the label-free sample by a first light pulse saturating a vibrational and/or electronic transition, said light pulse presenting an intensity spatial distribution on the sample presenting at least one minimum wherein saturation does not occur, and
    measuring the local absorbance properties and/or the local second order non-linear susceptibility of the sample by using a second light pulse forming the light probe at a wavelength corresponding to said electronic and/or vibrational transition, wherein the second light pulse overlap said first light pulse intensity minimum.

2. The method according to claim 1 wherein the second light pulse is timely separated from the first light pulse and illuminates the sample before the relaxation of the vibrational and/or electronic transition saturation occurs.

3. The method according to claim 1 wherein the first and second light pulses present different polarization, and the measurement of the local absorbance properties and/or the local second order non-linear susceptibility of the sample comprises the step of filtering out the polarized signal arising from the first light pulse by means of a polarizing filter.

4. The method of claim 1 wherein the first and second light pulses are angularly separated so that the signal arising from the first and second light pulses are angularly separated.

5. The method of claim 1 wherein the second light pulse is separated from the first light pulse by means of time-gating.

6. The method of claim 1, wherein the transition is non-fluorescent.

7. The method of claim 1, wherein the first and second light pulses are infrared light pulses having a wavelength comprised between 1 and 50 µm.

8. The method according to claim 1, wherein the second light pulse have a wavelength equal to the wavelength of the first light pulse.

9. The method according to claim 1 wherein the intensity minimum of the first light pulse is induced by an interference device producing at least one intensity node.

10. The method according to claim 1 wherein said method is repeatedly applied at a repetition rate lower than 10 MHz.

11. The method according to claim 1 wherein the sample or the repeated first and second light pulse is/are scanned in two directions on the sample surface to be able to reconstruct an image of the absorbance and/or second order susceptibility of the sample surface.

12. The method according to claim 1 wherein, analyzing the sample comprises the step of determining local chemical properties of the sample from the measurement of the local light absorption.

13. The method of claim 1, wherein the sample is further illuminated by visible light and wherein the detection is performed by Sum-Frequency Generation (SFG) or wherein the detection is performed by IR absorption spectroscopy.

14. A microscope comprising:
 at least one light source able to illuminate a region of interest of a label-free sample by a first and a second light pulse, said first light pulse being able to saturate a vibrational and/or electronic transition,
 a first optical lens arranged so that the first light pulse presents, in use, at least one minimum of light intensity on the sample,
 a second optical lens arranged so that the second light pulse overlap said at least one minimum,
 a detector for determining absorbance and/or second order non-linear susceptibility of the sample using the second light pulse,
 wherein said second light pulse having a wavelength corresponding to said vibrational and/or electronic transition, and wherein the signal arising from the first light pulse on the detector is reduced in use by timely separating, angularly separating and/or polarizing in different directions, the first and second light pulses or by using slightly different wavelength of the first and second light pulses.

15. The microscope of claim 14 wherein the at least one light sources is arranged so that the first and second light pulses are timely separated when reaching the sample surface.

16. The microscope of claim 14, wherein said at least one light source comprises at least one pulsed laser.

17. The microscope of claim 14 wherein the first optical lens comprise an interfering device in the form of a vortex wave plate on the optical path of the first light pulse for inducing light intensity minima of the first light pulse on the sample and/or wherein the first and second light pulses consist of infrared light.

18. The microscope of claim 14 wherein the first and second light pulses are infrared light pulses and the microscope further comprises a visible light source for determining the second order non-linear susceptibility of the sample by measuring a sum frequency generation signal.

19. The microscope of claim 14 further comprising a scanner for synchronously displacing the intensity minimum of the first light pulse and the position of the second light pulse and/or comprising a scanner for synchronously displacing the sample in the laser beams.

20. The microscope of claim 14, wherein the at least one light source comprises one pulsed laser, a beam splitter device in the form of a partially reflective mirror, or a polarizing beam splitter for splitting each laser pulse into said first and second light pulse, the second light pulse being delayed by optical means from the first light pulse for sequentially illuminating the region of interest by the first and second light pulse.

* * * * *